United States Patent [19]

Parry et al.

[11] Patent Number: 4,654,332

[45] Date of Patent: * Mar. 31, 1987

[54] HETEROCYCLIC COMPOUNDS

[75] Inventors: Keith P. Parry, Maidenhead; William G. Rathmell, Wokingham; Paul A. Worthington, Maidenhead, all of England

[73] Assignee: Imperial Chemical Industries PLC, London, England

[*] Notice: The portion of the term of this patent subsequent to Nov. 18, 2003 has been disclaimed.

[21] Appl. No.: 124,253

[22] Filed: Feb. 25, 1980

[30] Foreign Application Priority Data

Mar. 7, 1979 [GB] United Kingdom ................. 7908003
Sep. 21, 1979 [GB] United Kingdom ................. 7932819

[51] Int. Cl.$^4$ ................. C07D 249/08; C07D 413/10; A01N 43/64; A01N 59/20
[52] U.S. Cl. .................................... 514/184; 514/383; 548/101; 548/262
[58] Field of Search ................ 548/262, 101; 424/269, 424/245; 514/184, 383

[56] References Cited

U.S. PATENT DOCUMENTS

| 4,085,209 | 4/1978 | Miller et al. | 514/399 |
| 4,113,465 | 9/1978 | Shephard et al. | 548/262 |
| 4,123,542 | 10/1978 | Walker | 514/399 |
| 4,243,405 | 1/1981 | Balasubramanyan et al. | 548/341 |
| 4,301,166 | 11/1981 | Regel et al. | 548/335 |
| 4,315,016 | 2/1982 | Balasubramanyan et al. | 514/383 |
| 4,358,458 | 11/1982 | Scharwachter et al. | 514/399 |
| 4,414,210 | 11/1983 | Miller et al. | 568/649 |

FOREIGN PATENT DOCUMENTS

| 2623129 | 11/1977 | Fed. Rep. of Germany | 548/341 |
| 7613372 | 6/1977 | Netherlands | 548/262 |

Primary Examiner—Glennon H. Hollrah
Assistant Examiner—D. L. Dinner
Attorney, Agent, or Firm—Cushman, Darby & Cushman

[57] ABSTRACT

Compounds of formula:

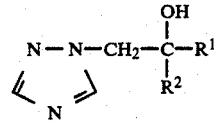

wherein $R^1$ is alkyl, cycloalkyl or phenyl and $R^2$ is phenyl or benzyl and their acid addition salts and metal complexes. The compounds have fungicidal activity.

10 Claims, No Drawings

HETEROCYCLIC COMPOUNDS

This invention relates to triazole compounds useful as fungicides, to a process for preparing them, to fungicidal compositions containing them, and to a method of combating fungal infections in plants using them.

The triazole compounds have the general formula (I):

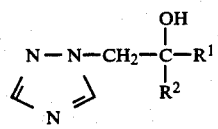

wherein $R^1$ is alkyl, cycloalkyl (e.g. cyclopentyl or cyclohexyl) or optionally substituted phenyl and $R^2$ is optionally substituted phenyl or optionally substituted benzyl; or an acid addition salt or metal complex thereof.

The compounds of the invention can contain chiral centres. Such compounds are generally obtained in the form of racemic mixtures. However, these and other mixtures can be separated into the individual isomers by methods known in the art.

The alkyl groups can be a straight or branched chain group having 1 to 6, e.g. 1 to 4, carbon atoms; examples are methyl, ethyl, propyl (n- or iso-propyl) and butyl (n-, sec-, iso- or t-butyl).

Examples of suitable substituents for the phenyl and for the phenyl moiety of the benzyl are halogen (e.g. fluorine, chlorine or bromine), $C_{1-5}$ alkyl [e.g. methyl, ethyl, propyl (n- or iso-propyl) and butyl (n-, sec-, iso- or t-butyl)], $C_{1-4}$ alkoxy (e.g. methoxy and ethoxy), trifluoromethyl, nitro, phenyl and phenoxy. The alkyl moiety of the benzyl can be substituted with for example one alkyl (e.g. methyl or ethyl). Suitably the phenyl and benzyl are unsubstituted or substituted with 1, 2 or 3 ring substituents as defined above. Preferably the benzyl and phenyl have a single ring substituent in the O-position. Examples of these groups are phenyl, benzyl, α-methylbenzyl, o-, m- or p-chlorophenyl, 2,4- or 2,6-dichlorophenyl, o-, m- or p-fluorophenyl, 2,6-difluorophenyl, o-, m- or p-bromophenyl, 2-chloro-4-fluorophenyl, 2-chloro-6-fluorophenyl, o-, m- or p-methoxyphenyl, 2,4-dimethoxyphenyl, o-, m- or p-ethoxyphenyl, o-, m- or p-nitrophenyl, o-, m- or p-methylphenyl, o-, m- or p-t-butylphenyl, o-, m- or p-trifluoromethylphenyl, o-, m- or p-phenoxyphenyl, and o-, m- or p-phenylphenyl (o-, m- or p-biphenylyl), and the corresponding ring substituted benzyl and α-methylbenzyl groups.

The salts can be salts with inorganic or organic acids e.g. hydrochloric, nitric, sulphuric, acetic, ptoluenesulphonic or oxalic acid.

Suitably the metal complex is one including, as the metal, copper, zinc, manganese or iron. It preferably has the general formula:

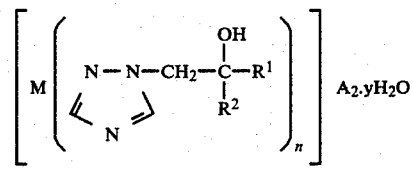

wherein Y, $R^1$ and $R^2$ are as defined above, M is a metal, A is an anion (e.g. a chloride, bromide, iodide, nitrate, sulphate or phosphate anion), n is 2 or 4 and y is 0 or an integer of 1 to 12.

Examples of the compounds of the invention are shown in Table I.

TABLE I

| COMPOUND NO | $R^1$ | $R^2$ | MELTING POINT (°C.) |
|---|---|---|---|
| 1 | $C_6H_5$— | $C_6H_5CH_2$— | 124–125 |
| 2 | $C_6H_5$— | p-Cl—$C_6H_4CH_2$— | 144–145 |
| 3 | $C_6H_5$— | p-F—$C_6H_4CH_2$— | 116–118 |
| 4 | p-Cl—$C_6H_4$— | p-Cl—$C_6H_4CH_2$— | 80–83 |
| 5 | p-Cl—$C_6H_4$— | $C_6H_5CH_2$— | 109–111 |
| 6 | p-F—$C_6H_4$— | $C_6H_5CH_2$— | 141–142 |
| 7* | $C_6H_5$— | 2,4-diCl—$C_6H_3CH_2$— | 104–106 |
| 8+ | p-F—$C_6H_4$— | p-F—$C_6H_4CH_2$— | 154–156 |
| 9 | p-F—$C_6H_4$— | p-Cl—$C_6H_4CH_2$— | 168–170 |
| 10 | t-Bu | $C_6H_5CH_2$— | 110–110 |
| 11 | t-Bu | p-Cl—$C_6H_4CH_2$ | 86–87 |
| 12 | t-Bu | p-F—$C_6H_4CH_2$— | 146–148 |
| 13 | $C_6H_5$— | o-F—$C_6H_4CH_2$— | 133–134 |
| 14 | p-Cl—$C_6H_4$— | o-F—$C_6H_4CH_2$— | 95–96 |
| 15 | $C_6H_5$— | o-Cl—$C_6H_4CH_2$ | 69–71 |
| 16 | p-MeO—$C_6H_4$— | $C_6H_5CH_2$ | 100–103 |
| 17 | $C_6H_5$— | $C_6H_5$— | 128–129 |
| 18+ | p-F—$C_6H_4$— | p-F—$C_6H_4CH_2$— | 161–163 |
| 19 | $C_6H_5$— | 2,4-diCl—$C_6H_3CH_2$— | 104–106 |
| 20 | t-Bu | o-Cl—$C_6H_4CH_2$— | 74–75 |
| 21 | t-Bu | o-F—$C_6H_4CH_2$— | 96–98 |
| 22 | t-Bu | m-Cl—$C_6H_4CH_2$— | 88–89 |
| 23 | t-Bu | m-$CF_3$—$C_6H_4CH_2$— | 106–107 |
| 24 | $C_6H_5$— | p-t-Bu—$C_6H_4CH_2$— | 80–83 |
| 25 | p-Cl—$C_6H_4$— | $C_6H_5$— | 83–85 |
| 26 | p-Cl—$C_6H_4$— | p-Cl—$C_6H_4$— | 147–148 |
| 27 | p-Cl—$C_6H_4$— | p-F—$C_6H_4$— | 154–155 |
| 28 | 2,4-diCl—$C_6H_3$— | $C_6H_5$— | 191–194 |
| 29 | p-F—$C_6H_4$— | p-F—$C_6H_4$— | 170–171 |
| 30 | p-F—$C_6H_4$— | $C_6H_5$— | 139–140 |
| 31 | i-Bu | $C_6H_5$— | 94–95 |
| 32 | n-Bu | p-Cl—$C_6H_5$— | 95–97 |
| 33 | t-Bu | 2-Cl—6-F—$C_6H_3CH_2$— | |

TABLE I-continued

| COMPOUND NO | R¹ | R² | MELTING POINT (°C.) |
|---|---|---|---|
| 34 | t-Bu | 2-Cl—4-F—C₆H₃CH₂— | |
| 35 | t-Bu | 2-F—4-Cl—C₆H₃CH₂— | |
| 36 | t-Bu | 2,4-diCl—C₆H₃CH₂— | |
| 37 | t-Bu | 2,6-diCl—C₆H₃CH₂— | |
| 38 | t-Bu | 2,6-diF—C₆H₃CH₂— | |
| 40 | C₆H₅— | p-t-Bu—C₆H₄ | |
| 41 | C₆H₅— | o-Cl—C₆H₄— | |
| 42 | C₆H₅— | o-F—C₆H₄— | |
| 43 | p-Cl—C₆H₄— | o-Cl—C₆H₄— | |
| 44 | p-Cl—C₆H₄— | o-F—C₆H₄— | |
| 45 | p-F—C₆H₄— | o-Cl—C₆H₄— | |
| 46 | p-F—C₆H₄— | o-F—C₆H₄— | |
| 47 | C₆H₅— | o-C₆H₅—C₆H₄— | |
| 48 | p-Cl—C₆H₄— | o-C₆H₅—C₆H₄— | |
| 49 | C₆H₅— | o-C₆H₅O—C₆H₄— | |
| 50 | p-Cl—C₆H₄— | o-C₆H₅O—C₆H₄— | |
| 51 | C₆H₅— | o-Me—C₆H₄— | |
| 52 | p-Cl—C₆H₄— | o-Me—C₆H₄— | |

*Includes 1 mole of ethanol occluded in the crystal lattice
+Compounds 8 and 18 were obtained as polymorphs and this explains their different methy points The compounds of general formula (I) may be produced by reacting a compound of general formula (II) or (III):

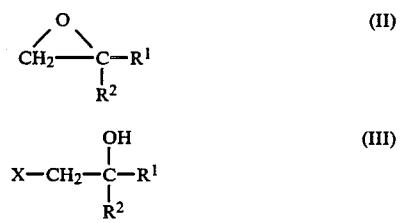

in which R¹ and R² are as defined above and X is a halogen atom (preferably a chlorine or bromine atom), with 1,2,4-triazole either in the presence of an acid-binding agent or in the form of one of its alkali metal salts in a convenient solvent. Suitably the compound of general formula (II) or (III) is reacted at 20°–100° C. with the sodium salt of 1,2,4-triazole (the salt can be prepared by adding either sodium hydride or sodium methoxide to 1,2,4-triazole) in a convenient solvent such as acetonitrile, methanol, ethanol or dimethylformamide. The product can be isolated by pouring the reaction mixture into water and recrystallising the solid formed from a convenient solvent.

The compounds of general formula (II) and (III) can be prepared by reacting a compound of general formula (IVa) or (IVb):

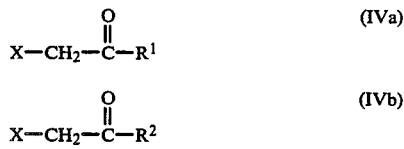

wherein R¹, R² and X are as defined above with, respectively, a Grignard compound of general formula (Va) or (Vb):

wherein R¹ and R² are as defined above and Y is a halogen (preferably chlorine, bromine or iodine) in a convenient solvent such as diethyl ether or tetrahydrofuran. Generally a mixture of the compounds of general formula (II) and (III) are obtained. For example, when a compound of general formula (IVa) wherein R¹ is alkyl or cycloalkyl is reacted, the compound of formula (II) generally predominates in the mixture; on the other hand, when R¹ is optionally substituted phenyl, the compound of general formula (III) generally predominates in the mixture.

The compounds of general formula (IV) and (V) may be made by methods set out in the literature.

The salts and metal complexes of the compounds of general formula (I) can be prepared from the latter in known manner. For example, the complexes can be made by reacting the uncomplexed compound with a metal salt in a suitable solvent.

The compounds, salts and metal complexes are active fungicides, particularly against the diseases:

*Piricularia oryzae* on rice

*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants

*Plasmopara viticola* on vines

*Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines

*Helminthosporium* spp. and *Rhynchosporium* spp. on cereals

*Cercospora arachidicola* on peanuts and other *Cercospora* species on for example sugar beet, bananas and soya beans *Botrytis cinerea* (grey mould) on tomatoes, strawberries, vines and other hosts

*Phytophthora infestans* (late blight) on tomatoes

*Venturia inaequalis* (scab) on apples.

Some of the compounds have also shown a broad range of activities against fungi in vitro. They have activity against various post-harvest diseases on fruit (e.g. *Penicillium digatatum* and *italicum* on oranges and *Gloeosporium musarum* on bananas). Further some of the compounds are active as seed dressings against: *Fusarium* spp., *Septoria* spp., *Tilletia* spp. (i.e. bunt, a seed borne disease of wheat), *Ustilago* spp., Helminthosporium spp. on cereals, *Rhizoctonia solani* on cotton and *Corticium sasakii* on rice.

The compounds can move acropetally in the plant tissue. Moreover, the compounds can be volatile enough to be active in the vapour phase against fungi on the plant.

The compounds may be used as such for fungicidal purposes but are more conveniently formulated into compositions for such usage. The invention thus provides also a fungicidal composition comprising a compound of general formula (I) or a salt or complex thereof as hereinbefore defined, and a carrier or diluent.

The invention also provides a method of combating fungal diseases in a plant, which method comprises applying to the plant, to seed of the plant or to the locus of the plant or seed a compound or a salt or complex thereof as hereinbefore defined.

The compounds, salts and complexes can be applied in a number of ways, for example they can be formulated or unformulated, directly to the foliage of a plant, to seeds or to other medium in which plants are growing or are to be planted, or they can be sprayed on, dusted on or applied as a cream or paste formulation, or they can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound, are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). These concentrates suitably contain organic acids (e.g. alkaryl or aryl sulphonic acids such as xylenesulphonic acid or dodecylbenzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal activity or compounds having plant growth regulating, herbicidal or insecticidal activity.

The other fungicidal compound can be for example one which is capable of combating ear diseases of cereals (e.g. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim (BCM), thiophanatemethyl, captafol, captan, sulphur, dithiocarbamates, carbathiins, copper oxychloride, triforine, dodemorph, tridemorph, dithianon, pyrazophos, binapacryl, quinomethionate, panoctine, furalaxyl, aluminium tris(ethylphosphonate), DPX3217, ethirimol, dimethirimol, bupirimate, chlorothalonil, Chevron RE 20615, vinclozolin, procymidone, iprodione, metaxanine, dichlobutrazol and thiabendazol.

The compounds of general formula (I) can be mixed with soil, peat or other rooting media for the protection of plants against seed-borne, soil-borne or foliar fungal diseases.

Suitable insecticides are pirimor, croneton, dimethoate, metasystox and formothion.

Examples of suitable plant growth regulating compounds are the gibberellins (e.g. GA$_3$, GA$_4$ or GA$_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or BAP), phenoxyacetic acids (e.g. 2,4-D or MCPA), substituted benzoic acids (e.g. TIBA), morphactins (e.g. chlorfluorecol), maleic hydrazide, glyphosate, glyphosine, long chain fatty alcohols and acids (e.g. Off Shoot O or Off Shoot T), dikegulac, Sustar, Embark, substituted quaternary ammonium and phosphonium compounds (e.g. CCC or PhosfonD), Ethrel, carbetamide, Racuza, Alar, asulam, abscissic acid, isopyrimol, RH531, hydroxybenzonitriles (e.g. bromoxynil), Avenge, Suffix or Lontrel.

The following Examples illustrate the invention; the temperatures are given in degrees Centigrade (°C.).

EXAMPLE 1

1-(1,2,4-Triazol-1-yl)-2,3-diphenyl-propan-2-ol

Benzyl chloride (0.2 mol) was dissolved in dry diethyl ether (200 ml) and added dropwise to magnesium turnings (0.22 g atoms). After all the magnesium had reacted, the solution was refluxed for 1 hour and cooled to room temperature. Phenacyl chloride (0.1 mol) in dry diethyl ether (100 ml) was added dropwise over 1 hour at such a rate as to maintain gentle reflux. The solution was then refluxed for 2 hours, and cooled to room temperature; the mixture was poured into ice and the complex decomposed with ammonium chloride solution. The ethereal solution was washed several times with water (2×200 ml), dried (Na$_2$SO$_4$), and the solvent removed in vacuo to give, as a colourless oil, the crude chlorohydrin which was dissolved in dimethyl formamide (80 ml) and a solution of sodium triazole [prepared from sodium (0.1 g atoms) in methanol (40 ml) and 1,2,4-triazole (0.1 mol)] added dropwise at room temperature. After stirring at room temperature for 2 hours, the solution was warmed at 50° for 3 hours. The solvent was removed in vacuo and the residue poured into water to give a crystalline solid which was recrystallised from ethanol/petroleum ether to give the title compound, m.p. 124.5°.

EXAMPLE 2

1-(1,2,4-Triazol-1-yl)-2-phenyl-3-p-fluorophenyl-propan-2-ol p-Fluorobenzyl chloride (0.1 mol) in dry diethyl ether (100 ml) was added dropwise to magnesium turnings (0.11 g atoms) and the solution stirred vigorously until, refluxing occurred. When all the magnesium had reacted, the solution was refluxed for a further 1 hour and then cooled to room temperature. Phenacyl chloride (0.05 mol) in dry diethyl ether (50 ml) was added dropwise to the solution over 1 hour at such a rate as to maintain gentle reflux. The mixture was refluxed for 2 hours, cooled to room temperature and the mixture poured into ice/ammonium chloride solution to decompose the complex. The ethereal solution was washed several times with water (2×200 ml), dried (Na$_2$SO$_4$), and the solvent removed in vacuo to give, as a colourless oil, the crude chlorohydrin. The latter was dissolved in dimethylformamide (40 ml) and a solution of sodium triazole [prepared from sodium (0.05 g atoms) in methanol (20 ml) and 1,2,4-triazole (0.05 mol)] added dropwise at room temperature. After stirring at room temperature for 2 hours, the solution, was warmed at 50° for 3 hours. The solvent was removed in vacuo and the mixture poured into water to give a crystalline solid which was recrystallised from petroleum ether/chloroform to give the title compound, m.p. 116°–8°.

EXAMPLE 3

1,1-Diphenyl-2-(1,2,4)-triazol-1-yl-ethan-1-ol

(Compound 17)

Stage 1. Bromobenzene (0.2 mol, 31.4 g) in sodium dry diethyl ether (200 ml) was added dropwise to magnesium (0.22 gram atoms, 5.3 g). After all the magnesium had reacted, phenacyl chloride (0.1 mol, 15.5 g) in diethyl ether (100 ml) was added dropwise and the solution stirred at room temperature for 1 hour. The reaction mixture was poured into saturated ammonium chloride solution, washed with water (3×150 ml), and dried (Na$_2$SO$_4$). Removal of the ether gave a pale yellow oil which solidified on standing. Recrystallisation from petroleum ether (60°–80°) gave 1,1-diphenyl-2-chloro-ethan-1-ol (60%) as a white crystalline solid, m.p. 56°–57°.

Stage 2. 1,2,4-Triazole (0.03 mol, 2.07 g) was added portionwise to a suspension of sodium hydride (0.03 mol, 0.72 g) in DMF (30 ml) and the solution stirred until effervescence ceased. 1,1-Diphenyl-2-chloro-ethan-1-ol (0.015 mol, 2.94 g) in dimethylformamide (DMF; 10 ml) was added dropwise and the solution warmed at 100° for six hours. The reaction mixture was poured into water and a white solid crystallised out. This was filtered off, washed with water, dried, and recrystallised from ethanol to give the title compound as a white crystalline solid, m.p. 128°–129°.

EXAMPLE 4

2-Methyl-4-phenyl-5-triazol-1-yl-pentan-4-ol (Compound 31)

Stage 1. The Grignard reagent generated from isobutyl bromide (0.1 mol, 13.7 g) in sodium dry diethyl ether (50 ml) and magnesium turnings (0.11 g atoms; 2.6 g) was added dropwise to a solution of phenacyl chloride (0.05 mol, 7.7 g) in sodium dry diethyl ether (100 ml) so that gentle reflux was maintained. The solution was then stirred at room temperature for 1 hour and the magnesium complex destroyed by pouring into a saturated ammonium chloride solution (200 ml). The ethereal extract was washed with water (3×150 ml) and dried ($Na_2SO_4$). Removal of the solvent gave a colourless liquid which distilled at reduced pressure to give 2-methyl-4-phenyl-5-chloro-pentan-4-ol (70%), b.p. 86°–88°/0.01 mm Hg.

Stage 2. 1,2,4-Triazole (0.03 mol, 2.07 g) was added portionwise to 100% sodium hydride (0.03 mol, 0.72 g) in dry DMF (30 ml) and stirred at room temperature until the effervescence ceased. 2-Methyl-4-phenyl-5-chloropentan-4-ol (0.01 mol, 2.1 g) in dry DMF (10 ml) was added dropwise at room temperature and then the solution was stirred at 100° for 6 hours. On cooling to room temperature the solution was poured into water to precipitate out a solid which was recrystallised from petroleum (60°–80°)/chloroform giving the title compound (60%) as a white crystalline solid, m.p. 94°–95°.

EXAMPLE 5

The compounds were tested against a variety of foliar fungal diseases of plants. The technique employed was as follows.

The plants were grown in John Innes Potting Compost (No. 1 or 2) in 4 cm diameter minipots. A layer of fine sand was placed at the bottom of the pots containing the dicotyledonous plants to facilitate uptake of test compound by the roots. The test compounds were formulated either by bead milling with aqueous Dispersol T or as a solution in acetone or acetone/ethanol which was diluted to the required concentration immediately before use. For the foliage diseases, suspensions (100 ppm active ingredient) were sprayed on to the soil. Exceptions to this were the tests on *Botrytis cinerea*, *Plasmopara viticola* and *Venturia inaequalis*. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the diseases. An exception was the test on *Erysiphe graminis* in which the plants were inoculated 24 hours before treatment. After inoculation, the plants were put into an appropriate environment to allow infection to take place and then incubated until the disease was ready for assessment. The period between inoculation and assessment varied from four to fourteen days according to the disease and environment.

The disease control was recorded by the following grading:

4=no disease
3=trace - 5% of disease on untreated plants
2=6–25% of disease on untreated plants
1=26–59% of disease on untreated plants
0=60–100% of disease on untreated plants.

The results are shown in Table II.

TABLE II

| COMPOUND NUMBER | PUCCINIA RECONDITA (WHEAT) | ERYSIPHE GRAMINIS (BARLEY) | PIRICULARIA ORYZAE (RICE) | PLASMOPARA VITICOLA (VINE) | PHYTOPHTHORA INFESTANS (TOMATO) | BOTRYTIS CINEREA (TOMATO) | CERCOSPORA ARACHIDICOLA (PEANUT) | VENTURIA INEQUALIS (APPLE) |
| --- | --- | --- | --- | --- | --- | --- | --- | --- |
| 1 | 4 | 4 | 1 | 0 | 0 | 3 | 4 | 3 |
| 2 | 4 | 4 | 0 | 0 | 0 | 3 | 3 | |
| 3 | 4 | 4 | 1 | 0 | 0 | 3 | 4 | 3 |
| 4 | 3 | 4 | 0 | 4 | 0 | 3 | 4 | 3 |
| 5 | 4 | 4 | 1 | 4 | 0 | 3 | 3 | 4 |
| 6 | 4 | 4 | 3 | 2 | 0 | 3 | 4 | |
| 7 | 4 | | 0 | 0 | 3 | 3 | 4 | 3 |
| 8 | 4 | | 3 | 4 | 3 | 3 | 4 | 3 |
| 9 | 3 | 4 | 2 | 0 | 0 | 2 | 3 | 3 |
| 10 | 4 | 4 | 3 | 0 | | 3 | 4 | 4 |
| 11 | 4 | 4 | 3 | 0 | 1 | 4 | 4 | 4 |
| 12 | 4 | 4 | | 0 | 0 | 4 | 4 | 4 |
| 13 | 4 | 4 | 3 | 3 | 0 | 3 | 4 | 3 |
| 14 | 4 | 4 | 1 | 0 | 1 | 4 | 4 | 3 |
| 15 | 4 | 4 | 1 | 0 | 2 | 3 | 4 | 3 |
| 16 | 4 | 4 | 4 | 0 | 0 | 3 | 4 | 0 |
| 17 | | 4 | | 0 | 0 | 1 | 4 | 4 |
| 18 | 4 | | 3 | 0 | 0 | 3 | 4 | 3 |
| 19 | 4 | 4 | 3 | 3 | 0 | | 4 | 4 |
| 20 | 4 | 4 | 4 | 0 | 0 | 3 | 4 | 3 |
| 21 | 4 | 4 | 3 | 1 | 0 | 4 | 4 | 4 |
| 22 | 4 | 4 | 4 | 0 | 2 | 3 | 4 | 4 |
| 23 | 4 | 4 | 3 | 0 | 0 | 3 | 4 | 4 |
| 24 | | 4 | 3 | 2 | 0 | 0 | 0 | 2 |
| 25 | 4 | 4 | 2 | 0 | 0 | 3 | 4 | 4 |
| 26 | 3 | 4 | 2 | 4 | 0 | 3 | 4 | 4 |
| 27 | 4 | 4 | 3 | 1 | 0 | 4 | 4 | 4 |
| 28 | 4 | 4 | 2 | 0 | 0 | 4 | | |
| 29 | | 4 | 3 | 0 | 0 | 3 | 4 | 4 |

TABLE II-continued

| COMPOUND NUMBER | PUCCINIA RECONDITA (WHEAT) | ERYSIPHE GRAMINIS (BARLEY) | PIRICULARIA ORYZAE (RICE) | PLASMOPARA VITICOLA (VINE) | PHYTOPHTHORA INFESTANS (TOMATO) | BOTRYTIS CINEREA (TOMATO) | CERCOSPORA ARACHIDICOLA (PEANUT) | VENTURIA INEQUALIS (APPLE) |
|---|---|---|---|---|---|---|---|---|
| 30 |  | 4 | 3 | 0 | 0 | 3 | 4 | 4 |
| 31 | 4 | 4 | 2 | 0 | 0 | 0 | 3 | 4 |
| 32 | 3 | 4 | 0 |  | 0 | 2 | 4 | 4 |

We claim:

1. A compound of general formula (I)

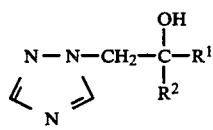

wherein $R^1$ is alkyl of 1-6 carbons, cycloalkyl of up to six carbons and $R^2$ is selected from the group consisting of benzyl, benzyl which is substituted in its phenyl moiety with halogen, $C_{1-5}$ alkyl, $C_{1-4}$ alkoxy, trifluoromethyl, nitro, phenyl or phenoxy, and benzyl substituted in its alkyl moiety with methyl or ethyl;

or an acid addition salt or copper, zinc, manganese or iron complex thereof.

2. A compound of general formula (I)

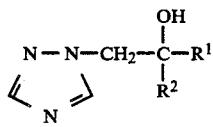

wherein $R^1$ is alkyl of 1-6 carbons, cyclopentyl or cyclohexyl and $R^2$ is selected from the group consisting of benzyl and benzyl which is substituted in its phenyl moiety with halogen, $C_{1-5}$ alkyl, $C_{1-4}$ alkoxy, trifluoromethyl, nitro, phenyl or phenoxy, and benzyl substituted in its alkyl moiety with methyl or ethyl; or an acid addition salt or copper, zinc, manganese or iron complex thereof.

3. A fungicidal composition consisting essentially of a fungicidally effective amount of a compound, salt or complex as claimed in claim 1, and a carrier or diluent.

4. A method of combatting fungal diseases in a plant, which method consists essentially of the step of applying to the plant, to seed of the plant or to the locus of the plant or seed an effective amount of the compound, salt or complex according to claim 1.

5. A compound according to claim 2 wherein $R^1$ is alkyl of 1-6 carbons and $R^2$ halo-benzyl.

6. A compound as claimed in claim 2 wherein $R^1$ is $C_{1-4}$ alkyl and $R^2$ is optionally substituted benzyl.

7. A compound as claimed in claim 2 wherein $R_1$ is butyl.

8. A compound as claimed in claim 7 wherein $R^1$ is t-butyl.

9. A fungicidal composition consisting essentially of a fungicidally effective amount of a compound, salt or complex as claimed in claim 2, and a carrier or diluent.

10. A method of combatting fungal diseases in a plant, which method consists essentially of the step of applying to the plant, to seed of the plant or to the locus of the plant or seed an effective amount of the compound, salt or complex according to claim 2.

* * * * *